United States Patent [19]

Baldenius et al.

[11] Patent Number: 6,005,122
[45] Date of Patent: Dec. 21, 1999

[54] PREPARATION OF α-TOCOPHEROL OR α-TOCOPHERYL ACETATE BY REACTING TRIMETHYLHYDROQUINONE AND PHYTOL OR ISOPHYTOL, WITH RECYCLING OF THE ZINC HALIDE CONDENSATION CATALYST

[75] Inventors: Kai-Uwe Baldenius, Frankenthal; Wulf Kaiser, Bad Dürkheim; Bernhard Bockstiegel, Römerberg; Harald Laas, Maxdorf; Bernhard Schulz, Schwetzingen; Peter Schmitt; Helmut Glietenberg, both of Ludwigshafen, all of Germany

[73] Assignee: BASF Aktiengesellschaft, Ludwigshafen, Germany

[21] Appl. No.: 08/990,092

[22] Filed: Dec. 12, 1997

[51] Int. Cl.$^6$ .................................................. C07D 311/72
[52] U.S. Cl. ........................... 549/410; 549/411; 549/412
[58] Field of Search .................................... 549/410, 411, 549/412

[56] References Cited

U.S. PATENT DOCUMENTS

| 2,411,969 | 12/1946 | Karrer et al. . | |
|---|---|---|---|
| 3,708,505 | 1/1973 | Greenbaum et al. | 260/345.5 |
| 4,191,692 | 3/1980 | Grafen et al. . | |
| 4,217,285 | 8/1980 | Yoshino et al. . | |
| 4,239,691 | 12/1980 | Nelan et al. . | |
| 5,532,387 | 7/1996 | Matsui et al. . | |
| 5,536,852 | 7/1996 | Matsui et al. . | |
| 5,610,113 | 3/1997 | Matsui et al. . | |

FOREIGN PATENT DOCUMENTS

| 0 100 471 | 2/1984 | European Pat. Off. . |
|---|---|---|
| 0 694 541 | 1/1996 | European Pat. Off. . |

OTHER PUBLICATIONS

Makoto Matsui, et al.; Synthesis of a–Tocopherol: Scandium (III) Trifluoromethanesulfonate as an Efficient Catalyst in the Reaction of Hydroquinone with Allylic Alcohol; Bull. Chem. Soc. Jpn., 68, 3569–3571 (1995).

Makoto Matsui, et al.; Bull. Chem. Soc. Jpn. 69, 137–139 (1996); Metal Ion–Exchanged Montmorillonites as Practical and Useful Solid Catalysts for the Synthesis of a–Tocopherol.

Weast, Robert, Ed. in Chief, CRC Handbook of Chemistry and Physics, 64$^{TH}$ edition, 1983–84.

*Primary Examiner*—Joseph K. McKane
*Assistant Examiner*—Tadfiq A. Solola
*Attorney, Agent, or Firm*—Oblon, Spivak, McClelland, Maier & Neustadt, P.C.

[57] ABSTRACT

A process for preparing α-tocopherol or α-tocopheryl acetate by reacting 2,3,5-trimethylhydroquinone with isophytol or phytol in the presence of a zinc halide condensation catalyst and a proton donor in a solvent with or without subsequent esterification with acetic anhydride, which comprises A. carrying out the reaction in a nonpolar solvent which is only slightly water-miscible, if at all and B. introducing the required zinc halide into the reaction in the form of a mixture of from 1 to 4 mol of water per mol of zinc halide.

The possibility of introducing the zinc halide required in the process according to the invention in the form of a mixture of zinc halide and water which can be readily handled and metered at from 50 to 200° C. without impairing the yield and purity of the tocopherol opens the way to an advantageous recycling of the zinc halide after the reaction by separating off or extracting and recycling the zinc halide in the form of a from 60 to 90% strength by weight solution or pumpable magma.

12 Claims, No Drawings

PREPARATION OF α-TOCOPHEROL OR α-TOCOPHERYL ACETATE BY REACTING TRIMETHYLHYDROQUINONE AND PHYTOL OR ISOPHYTOL, WITH RECYCLING OF THE ZINC HALIDE CONDENSATION CATALYST

The invention relates to an improved process for preparing α-tocopherol or α-tocopheryl acetate by reacting 2,3,5-trimethylhydroquinone (TMH) with a phytol, in particular isophytol (IP) in the presence of a zinc halide, a proton donor in the presence or absence of an amine in a solvent at elevated temperature with or without subsequent esterification with acetic anhydride, with recycling of the zinc halide condensation catalyst. For the purposes of the invention, zinc halide condensation catalysts are essentially the halides zinc chloride and zinc bromide which can be obtained inexpensively, but also mixtures thereof and mixtures thereof with basic chlorides and bromides of zinc, ie. oxy- and hydroxyhalides.

In recent years, α-tocopherol (vitamin E) has become of increasing importance as an antioxidant and in the field of human and animal nutrition. Numerous processes have therefore been developed for its synthesis. A review by Siebrell and Harris can be found in "The Vitamins", Vol V, pages 168 ff. (1972).

On an industrial scale, it has proved useful to prepare vitamin E by condensing TMH with IP in a solvent in the presence of Lewis acids, in particular zinc chloride, together with a proton donor, in particular hydrogen chloride gas, at elevated temperature (cf. U.S. Pat. No. 2,411,969 of Hoffmann-La Roche, U.S. Pat. No. 4,239,691 of Eastman Kodak, U.S. Pat. No. 3,708,505 of Diammond Shamrock and DE 3 203 487 of BASF).

A wide range of solvents can be used for this reaction, eg. ethyl acetate, acetic acid, aliphatic or aromatic hydrocarbons or chlorinated hydrocarbons.

According to DE 26 06 830 and EP 100 471, particularly good yields and particularly pure vitamin E are produced in this reaction if it is carried out, in addition, in the presence of small amounts of an amine or an ammonium salt.

It is a disadvantage of this very good process per se that the customary use of relatively large amounts of $ZnCl_2$ cause great wastewater problems. A further great disadvantage in the use of zinc chloride for this reaction is, according to Bull. Chem. Soc. Jpn., 68 (1995) 3569–71, in particular 3569, left column, and Bull. Chem. Soc. Jpn. 69 (1996) 137–139, in particular 137, left column, that Lewis acids, such as zinc chloride, are deactivated by the water formed in the reaction.

Attempts to extract the zinc chloride with water from the reaction mixture and to recycle it to the reaction in the form of the resulting from 20 to 60% strength by weight solution led to poor yields and to less pure vitamin E. A separate work-up of the from 20 to 60% strength by weight zinc chloride solution to give dry zinc chloride powder and recycling the zinc chloride powder to the vitamin E synthesis cannot be carried out economically because of the high cost of equipment for working with a solid.

Because of these difficulties in working with zinc chloride, in the most recent literature, other acid catalysts have been described for the condensation of TMH and IP on an industrial scale. Thus, for example, in Bull. Chem. Soc. Jpn. 68 (1995) 3569 to 3571, scandium(III) trifluoromethanesulfonate and in Bull. Chem. Soc. Jpn. 69 (1996) 137–39, montmorillonites containing exchanged metal ions, are recommended as catalysts. DE-A 2 743 920 describes zinc chloride adsorbed onto silica gel/aluminum oxide as catalyst.

A disadvantage of these processes is that Sc(III) trifluoromethanesulfonate is very expensive and is not available in sufficient quantity, and the montmorillonites and the zinc chloride-silica gel/aluminum catalysts require complex solids handling for further use.

Customarily, when zinc chloride is used as a condensation agent, it is used as a solid powder. On an industrial scale, when a solid is introduced into a reaction vessel containing an organic solvent, such as heptane, considerable technical efforts must be made to prevent electrical charges and the formation of explosive mixtures, as well as to prevent the resulting explosion hazard.

It is an object of the present invention, therefore, to improve the method, which is proved in practice per se, for preparing vitamin E by condensing TMH with IP in a solvent in the presence of a zinc halide, a proton donor and in the presence or absence of an ammonium salt and/or an amine, in such a manner that the complex solids handling can be avoided without impairing yield and/or purity of the α-tocopherol or α-tocopheryl acetate. It is a further object of the present invention to improve the process in such a manner that the zinc halide and also as far as possible the ammonium salt and/or the amine can be recovered after the reaction in a simple and economic manner and can be recycled to the reaction.

We have found that this object is achieved, surprisingly, by the process for preparing α-tocopherol by reacting TMH with phytol or IP in the presence of zinc chloride or zinc bromide and a proton donor, in which process pure α-tocopherol is also obtained in very good yields by A. carrying out the reaction in a nonpolar solvent which is only slightly water-miscible, if at all and
B. introducing the required zinc chloride or zinc bromide into the reaction in the form of a mixture of from 1 to 4 mol of water per mol of zinc chloride or zinc bromide, preferably from 1 to 3 mol of water per mol of zinc chloride or zinc bromide, which corresponds industrially to from about 65 to 90% strength by weight, preferably from an about 70 to about 90% strength by weight possibly hot aqueous solution, supersaturated solution or pumpable magma.

It has further been found that this from about 65 to 90% strength by weight mixture of water and zinc chloride or zinc bromide can be transported and metered in a simple manner by appropriately heated piping at from 20 to 200° C., preferably from 50 to 200° C.

The present invention therefore relates to a process for preparing α-tocopherol or α-tocopheryl acetate by reacting 2,3,5-trimethylhydroquinone with phytol or isophytol in the presence of a zinc halide and a proton donor with or without subsequent esterification with acetic anhydride, which comprises A. carrying out the reaction in a nonpolar solvent which is only slightly water-miscible, if at all and
B. introducing the required zinc halide into the reaction in the form of a mixture of from 1 to 4 mol of water per mol of zinc halide, preferably from 1 to 3.5 mol of water per mol of zinc halide, in particular from 1 to 3 mol of water.

Very particular advantages are provided by the possibility of being able to introduce into the reaction, in the process according to the invention, the zinc halide required in the form of a readily handleable mixture of from 1 to 4 mol of water per mol of zinc halide, for recycling the zinc halide after the reaction is complete.

The process according to the invention takes place particularly advantageously if the zinc halide used is one of the halides zinc chloride or zinc bromide which can be obtained inexpensively.

The present invention therefore also relates to a process for preparing α-tocopherol or α-tocopheryl acetate by reacting TMH with phytol or IP in the presence of zinc chloride or zinc bromide and a proton donor in a solvent with or without subsequent esterification with acetic anhydride, which comprises A. carrying out the reaction in a nonpolar solvent which is only slightly water-miscible, if at all, B. after completing the reaction, separating off the zinc chloride or zinc bromide and/or extracting it from the resulting tocopherol solution with water or a mixture of water and a low-boiling water-miscible organic solvent and C. partly or completely recycling the zinc chloride or zinc bromide solution obtained, with or without concentration, in the form of a from about 60 to 90% strength by weight possibly hot solution or pumpable magma to the reaction process in such a manner that, after making up the zinc chloride or zinc bromide still missing, not more than 4 mol of water, preferably not more than 3.5 mol of water, in particular not more than 3 mol of water, per mol of zinc chloride or zinc bromide are present in the reaction mixture for the following reaction.

Recycling the zinc chloride or zinc bromide solution after concentration in the form of a solution or pumpable magma in place of zinc chloride or zinc bromide powder is possible if, in process step C., the aqueous zinc chloride or zinc bromide solution, after concentration to about from 60 to 90% by weight of zinc chloride or zinc bromide, preferably from 70 to 90% by weight of zinc chloride or zinc bromide, is kept at from 20 to 200° C., preferably from 50 to about 200° C., and/or is recycled to the reaction process by appropriately heated piping.

Suitable solvents which are only slightly water-miscible, if at all, for the process according to the invention are, in particular, hydrocarbons having a boiling point or boiling range of from 60 to 200° C., such as hexane, heptane, cyclohexane, octane, nonane, decane, decalin, toluene, xylene or chlorobenzene, or mixtures of two or more of these, such as petroleum ether. Particularly advantageously, the operations are carried out in heptane. However, in principle, tocopherol itself can serve as nonpolar solvent.

Suitable low-boiling water-miscible organic solvents for the extraction are, for example, methanol, ethanol, tetrahydrofuran and acetone. Particularly advantageously, methanol is employed, since, in the presence of water, this is virtually insoluble in the hydrocarbons used for the extraction. Generally, the low-boiling water-miscible solvent is employed in a weight ratio of water to solvent of from about 4:1 to 1:10.

In a possible advantageous embodiment of the process according to the invention with recycling of zinc chloride or zinc bromide,
in process step B., the majority of the zinc chloride or zinc bromide is extracted from the tocopherol solution using very little water, and in
process step C., sufficient of the resulting aqueous solution or pumpable magma is recycled to the reaction process for the following reaction so that, after making up the zinc chloride or zinc bromide still missing using anhydrous zinc chloride or zinc bromide or a from 85 to 90% strength by weight solution or pumpable magma, not more than 4, preferably not more than 3 mol of water per mol of zinc chloride or zinc bromide are present in the reaction mixture for the following reaction.

A further advantageous embodiment of the process according to the invention is that in process step B., the zinc chloride or zinc bromide is removed as completely as possible from the tocopherol solution by repeated extraction with water or a mixture of water and methanol with or without about 0.5 to 1% by weight of an added mineral acid, preferably HCl, and in process step C., the resulting dilute zinc chloride or zinc bromide solution is concentrated by evaporating water or methanol and water to the extent that the zinc chloride or zinc bromide solution or pumpable magna contains no more than 4 mol of water, preferably not more than 3.5, in particular not more than 3 mol of water, per mol of zinc chloride or zinc bromide and it is recycled in this state to the reaction process.

Adding the mineral acid to the water used for the extraction is intended to ensure that even in the case of repeated extraction the customary and advantageous pH range (below 5) is maintained.

The repeated extraction is advantageously carried out by means of a from 1- to 3-stage countercurrent extraction.

In this case, the resulting dilute zinc chloride or zinc bromide solution can first be concentrated in a special distillation apparatus in the presence or absence of a suitable azeotrope former and then recycled to the reaction process in the form of a possibly hot solution or pumpable magma, or else concentrated in the reaction vessel itself in the presence or absence of a suitable azeotrope former before adding IP.

If α-tocopherol or α-tocopheryl acetate is prepared, as described in DE 26 06 830 or EP 100 471, in the presence of an ammonium salt and/or an amine, it is even possible, in process step B. after the reaction, to extract the zinc chloride or zinc bromide together with any ammonium salt and/or amine as well as unreacted TMH present from the resulting tocopherol solution using a mixture of water and methanol in a ratio of from about 4:1 to 1:10 and to recycle the resulting extract, after concentration, in the form of a possibly hot solution or pumpable magma to the reaction process in such a manner that in the reaction mixture for the following reaction, not more than 4 mol of water, preferably not more than 3 mol of water are present per mol of zinc chloride or zinc bromide.

The isophytol or phytol, which may have been treated in accordance with DE 2 606 830 with an ammonium salt and/or an amine, is reacted with TMH in a manner known per se at from 60 to 200° C., preferably at from 80 to 140° C., in particular at from 90 to 110° C., and in the above-described hydrocarbons as solvents. The amount of solvent can be varied within broad ranges, it can be from one to ten times the amount by weight of the IP. The amount of zinc chloride or zinc bromide can be 0.04 parts by weight of the IP up to very high amounts of 0.5 parts by weight and above, but this gives no advantage.

Proton donors which can be used are mineral acids, such as concentrated hydrochloric acid, concentrated hydrobromic acid, sulfuric acid, phosphoric acid or sodium hydrogensulfate. Of these, hydrochloric acid is preferred.

In addition, toluenesulfonic acid or trifluoromethanesulfonic acid can be used, and also mixtures of said acids.

The water formed in the reaction can be removed, but the reaction in specific cases can also be carried out without removal of water.

Instead of adding aqueous hydrochloric acid, the procedure may be advantageously carried out with introduction of hydrogen chloride gas. This has the advantage that the acid concentration cannot increase to an excessive value, since excess hydrogen chloride gas volatilizes from the reaction mixture. A high-boiling acid, such as sulfuric acid, can, in contrast, in excessive concentration favor the formation of by-products.

The reaction can be carried out batchwise or continuously.

The amount of water required for the extraction depends on the amount of zinc halide used, the amount of solvent used, the amount of water removed during the reaction, the number of extraction stages and on the desired degree of extraction for the zinc halide. It can therefore vary within broad limits. To extract only the majority of the zinc halide, generally a single wash with approximately from 3 to 10% by volume of water, based on the organic phase, is sufficient. For complete extraction, washing is performed from 2 to 6 times, each time using from 0.5 to 10% by volume of water or aqueous methanol, preferably from 2 to 4 times each time using from 1 to 5% by volume of water or aqueous methanol. Particularly advantageously, complete extraction is successfully performed in a three-stage countercurrent extraction using from 1 to 3% by volume of water.

However, the water formed in the reaction containing zinc chloride or zinc bromide can alternatively be removed as such.

When fresh dry zinc chloride or zinc bromide is additionally added, 60% strength by weight zinc chloride or zinc bromide solutions can also be recycled. If virtually complete recycling of the zinc halide is employed, only very small amounts being added, ie. only from about 0 to 3% of dry zinc chloride or zinc bromide in the form of a from 85 to 90% strength by weight solution, the zinc halide solutions or pumpable magma used as catalyst solution should contain at least 65% by weight of zinc chloride or zinc bromide, which corresponds to an amount of about 4 mol of water per mol of zinc chloride or zinc bromide. Advantageously, a catalyst solution or pumpable magma is employed which contains from 70 to 90% by weight, in particular from 80 to 90% by weight, of zinc halide, which corresponds roughly to amounts of from 1 to 3 mol of water, in particular from about 1 to 2 mol of water, per mol of zinc halide. The higher the content of zinc chloride or zinc bromide in the mixture, the more important it is to keep this mixture at from about 50 to 200° C., preferably from 80 to 200° C., during standing and/or during addition. At a zinc chloride or zinc bromide concentration above about 90% by weight, the risk of the solution, the supersaturated solution or magma solidifying increases, which would make the process procedure more difficult.

The examples illustrate the invention. The yields given apply to the pure active compound (vitamin E acetate 100% pure) and are based on TMH used. The purity was determined by gas-chromatographic analysis (GC) of the resulting product. The color of the distillate after the VEA distillation was measured by absorption spectroscopy (Perkin-Elmer 552; path length 1 cm pure substance; wavelength 420 nm) and the color intensity C.I. as calculated using the formula C.I.=−0.261 (% transmittance)+25.23.

COMPARATIVE EXAMPLES 1, 2b AND 2g AND EXAMPLES 2a, 2c to 2f AND 2h TO 2j

A 4 l stirred glass vessel equipped with an attached reflux condenser and water separator was charged in each case with 1170 g of heptane, 600 g of trimethylhydroquinone (TMH: purity>99%), 12 g of tridecylamine (TDA), the amount x[g] of anhydrous zinc chloride given in Table 1 and the amount y[g] of an aqueous zinc chloride solution of concentration z [% by weight] given in Table 1, and the batch was heated with stirring. Hydrogen chloride (approximately 20 g/h) was then added. 1210 g of isophytol (IP; 98% pure) were then added in the course of 1 hour (h) to the boiling mixture, with removal of water (W). The mixture was then allowed to react for a further 1 h at boiling temperature. It was then washed with 100 ml of W. From 98 to 100% of the zinc chloride used could be recovered with washing three times, each time using 100 ml of W. The mixture was then washed with aqueous methanol. After removal of the solvent, the crude α-tocopherol was esterified by refluxing with acetic anhydride and the resulting vitamin E acetate (VEA) was obtained in the yield of pure vitamin E acetate given in Table 1, based on TMH used, and in the purity (determined by GC) given in Table 1.

TABLE 1

| Ex. | Amount x of anhydrous $ZnCl_2$ [g] | Amount y of $ZnCl_2$ solution [g] | Conc. z of the $ZnCl_2$ solution [% by wt.] | Addition of water [mol/mol of $ZnCl_2$] | Yield [% of Theory] | Purity [%] |
|---|---|---|---|---|---|---|
| 1* | 125 | — | — | 0 | 97 | 97.7 |
| 2a | 100 | 68 | 56 | 1.6 | 95 | 97.5 |
| 2b* | 28 | 197 | 56 | 4.8 | 88 | 94.9 |
| 2c | 25 | 125 | 80 | 1.4 | 96 | 97.3 |
| 2d | — | 156 | 80 | 1.9 | 95 | 97.1 |
| 2e | — | 313 | 80 | 1.9 | 96 | 97.4 |
| 2f | 100 | 31 | 80 | 0.4 | 98 | 97.8 |
| 2g* | 250 | — | — | 0 | 96 | 96.7 |
| 2h | — | 175 | 72 | 3.0 | 97 | 97 |
| 2i | — | 191 | 65 | 4.0 | 93 | 95.5 |
| 2j | — | 764 | 65 | 4.0 | 90 | 96.0 |

*Comparative Examples

Examples 2a, 2c to 2f and 2h to 2j show the influence of W on the catalyst activity. When up to 3 mol of water are used conjointly per mol of $ZnCl_2$, no significant impairment of yield and purity is observed; from 4 mol of W per mol of $ZnCl_2$, the yields decrease slightly. Examples 2e and 2j and Comparative Example 2g show that higher amounts of catalyst do not give any further advantage.

EXAMPLE 3

Reaction in the Presence of Only a Little Anhydrous $ZnCl_2$ and Highly Dilute $ZnCl_2$ Solution A 4 l stirred glass vessel equipped with an attached reflux condenser and a) with a water separator and b) without a water separator was charged in each case with 1170 g of heptane, 600 g of TMH, 12 g of TDA and 23 g of anhydrous $ZnCl_2$ and also 463 g of an aqueous $ZnCl_2$ solution (concentration: 20% by weight; ratio of W/$ZnCl_2$=24 mol/mol) and the batch was heated with stirring and a) with removal of W and b) without removal of W and approximately 20 g/h of hydrogen chloride were added. 1210 g of IP were added to the boiling mixture in the course of 1 h and the reaction mixture was allowed to react for a further 2 h.

In reaction batch a), the reaction between TMH and IP began after the majority of the water had separated off from the $ZnCl_2$ solution in the water separator. The batch was worked up in a similar manner to Example 2.

In reaction batch b), the desired α-tocopherol was formed only in traces, which shows that relatively large amounts of W in the reaction mixture completely deactivate the catalyst.

The yields achieved in each case are given in Table 2, which shows that the yield and purity of the resulting tocopherol are poorer than in Example 4, which demonstrates that it is more advantageous to concentrate the catalyst solution as soon as before the reaction has begun.

TABLE 2

| Ex. | Amount x of anhydrous $ZnCl_2$ [g] | Amount y of $ZnCl_2$ solution [g] | Conc. z of the $ZnCl_2$ solution [% by wt.] | Input of W [mol of W/mol of $ZnCl_2$] | Yield [% of Theory] | Purity [%] |
|---|---|---|---|---|---|---|
| 3a* | 23 | 463 | 20 | 24 | 86 | 93.5 |
| 3b** | 23 | 463 | 20 | 24 | <5 | |

\* = with removal of W
\*\* = without removal of W

EXAMPLE 4

Reaction in the Presence of Only a Little Anhydrous $ZnCl_2$ and a Concentrated $ZnCl_2$ Solution The above-described 4 l stirred vessel was charged in each case with 1170 g of heptane, 600 g of TMH, 12 g of TDA, 23.2 g of anhydrous $ZnCl_2$ and 115.9 g of an 80% strength by weight $ZnCl_2$ solution and the batch a) was heated with removal of W and b) without removal of W. Approximately 20 g/h of hydrogen chloride were then added and 1210 g of IP were added to the boiling mixture in the course of 1 h. The mixture was then allowed to react for a further 1 h. The mixture was then washed once with 300 ml of W and 3× with aqueous methanol and esterified with acetic anhydride in a similar manner to Example 2.

The yields and purities achieved are given in Table 3:

TABLE 3

| Ex. | Anhydrous $ZnCl_2$ [g] | Amount y of $ZnCl_2$ solution [g] | Conc. z of the $ZnCl_2$ solution [% by wt.] | Input of W [mol of W/mol of $ZnCl_2$] | Yield [% of Theory] | Purity [%] |
|---|---|---|---|---|---|---|
| 4a* | 23.2 | 115.9 | 80 | 1.5 | 97 | 97.3 |
| 4b** | 23.2 | 115.9 | 80 | 1.5 | 97 | 97.5 |

\* = with removal of W
\*\* = without removal of W

Examples 4a and 4b show that with a water input rate of only 1.5 mol/mol of $ZnCl_2$, removing W can be omitted, without impairing yield and purity.

EXAMPLE 5

Multiple Recycling of $ZnCl_2$; Mean Degree of Recycling 78%

The above-described 4 l stirred vessel equipped with reflux condenser and water separator was charged with 1170 g of heptane, 600 g of TMH, 12 g of TDA and the amount x [g] of anhydrous $ZnCl_2$ given in Table 4 and the amount y [g] of $ZnCl_2$ solution given in Table 4 of concentration z given in Table 4 and the batch was heated with stirring. Approximately 20 g/h of hydrogen chloride gas were then added, 1210 g of IP were added to the boiling mixture in the course of 1 h, and the reaction mixture was then allowed to react for a further 1 h.

By a single addition of 100 ml of W, a majority (approximately 80%) of the $ZnCl_2$ was then extracted. The heptane/tocopherol phase was washed with aqueous methanol, concentrated by evaporation and the resulting crude tocopherol was esterified with acetic anhydride. The crude tocopherol acetate was distilled at $<10^{-2}$ mbar and approx. 200–250° C. in a bulb tube.

The resulting aqueous $ZnCl_2$ solution (approximately 200 g having a mean concentration of approximately 50% by weight of $ZnCl_2$) was concentrated in a Sambay evaporator to the concentration z given in Table 4. The concentrate was stored at 100° C. and did not solidify at these temperatures. It was reused as catalyst in the next condensation batch, in addition to the amount of anhydrous $ZnCl_2$ given in Table 4. In the same manner, the recovered $ZnCl_2$ was used in each case in 10 successive condensation batches. The W input in all batches was from about 1.0 to 1.2 mol of W per mol of $ZnCl_2$. Table 4 gives the reaction conditions and yields and purities of the vitamin E acetate obtained using recycled $ZnCl_2$.

TABLE 4

| Ex. | x anhydrous $ZnCl_2$ [g] | y $ZnCl_2$ solution [g] | z conc. of the $ZnCl_2$ solution [% by wt.] | Degree of recycling [%] | Yield [% of theory] | Purity [%] | Distillation residue [%] | Color of distillate [C.I] |
|---|---|---|---|---|---|---|---|---|
| 5 | 125 | — | — | — | 98 | 98.0 | 0.5 | 15 |
| 5.1 | 23 | 118 | 86.5 | 82 | 97 | 97.9 | 0.5 | 20 |
| 5.2 | 32.4 | 110.3 | 83.9 | 74 | 97 | 97.9 | 0.6 | 19 |
| 5.3 | 29.3 | 113.7 | 84.2 | 77 | 98 | 97.9 | 0.5 | 12 |
| 5.4 | 26.5 | 117.3 | 84.0 | 79 | 97 | 97.9 | 0.8 | 11 |
| 5.5 | 32.3 | 110.7 | 83.8 | 74 | 97 | 97.8 | 2.2 | 12 |
| 5.6 | 24.1 | 117.3 | 86.0 | 81 | 97 | 97.8 | 1.0 | 14 |
| 5.7 | 36.4 | 107.4 | 84.2 | 72 | 97 | 97.8 | 1.5 | 14 |
| 5.8 | 21.0 | 121.0 | 86.0 | 83 | 97 | 97.8 | 0.7 | 13 |
| 5.9 | 21.5 | 120.8 | 85.7 | 83 | 97 | 97.8 | 0.8 | 16 |
| 5.10 | 26.5 | 117.2 | 84.0 | 79 | 97 | 97.8 | 1.0 | 14 |
| Mean | | | 84.0 | 78 | 97 | 97.9 | 1.0 | 14 |

Examples 5 to 5.10 show that even after recycling ZnCl$_2$ solution of the concentration given 10 times in succession, no impairment in yield or purity of the VEAs prepared was observed. The formation of high-boiling minor components, which are produced as non volatile residue during a vacuum distillation of crude vitamin E acetate, and the color of the distillate (reported as Colour Intensity C.I.) remained without significant change.

EXAMPLE 6

Multiple Recycling of ZnCl$_2$; Mean Degree of Recycling>97%

In a similar manner to Example 5, 600 g of TMH in the presence of the amounts given by Table 5 x [g] of anhydrous ZnCl$_2$ and y [g] of a recycled aqueous ZnCl$_2$ solution having a concentration of z % by weight were reacted with 1210 g of IP to give α-tocopherol. After further reaction for 1 hour, the mixture was washed three times, each time with 100 ml of water, 98–100% of the ZnCl$_2$ used being recovered. After taking off the solvent, the crude α-tocopherol was esterified with acetic anhydride.

In this manner, from about 400 to 420 g of ZnCl$_2$ solution having a mean concentration of 30% by weight of ZnCl$_2$ were obtained each time. These solutions were filtered and concentrated on a Sambay evaporator. The concentrate was kept until reuse at 100° C., without it solidifying. As described above, it was used each time as catalyst for the following condensation batch.

The Examples 6 to 6.20 show that even after 20-fold recycling of ZnCl$_2$ solution of concentration z given in Table 5 neither was an impairment in yield and purity of the VEAs observed, nor did the proportion of nonvolatile residue in the VEA distillation or the color of the distillate increase.

EXAMPLE 7

Recycling ZnCl$_2$ with Concentration of the Catalyst Solution by Azeotropic Distillation in the Reaction Vessel A 0.5 l three-neck glass flask equipped with paddle agitator, dropping funnel, reflux condenser and water separator was charged with 150 g of heptane, 76 g of TMH, 1.5 g of TDA and 16 g of anhydrous ZnCl$_2$ and the batch was heated with stirring. Hydrogen chloride was added (approximately 5 g/h). 153 g of IP were added to the boiling mixture.

The mixture was allowed to react for a further 1 h. After cooling, 12.5 ml of water were added, the solution was mixed and, after standing, the phases were separated. The heptane phase was concentrated and the crude tocopherol was esterified with acetic anhydride by heating under reflux to give VEA.

The aqueous phase was charged as catalyst for the next experiment. 150 g of heptane, 76 g of TMH and 1.6 g of fresh zinc chloride were added and the batch was heated as above with stirring. The W was removed by azeotropic distillation with the heptane in the water separator and hydrogen chloride was added (approximately 5 g/h). After approximately 10 ml of the water had been removed, 153 g of IP were added to the boiling mixture. The mixture was allowed to react further. The work-up was performed as described above.

The ZnCl$_2$ was recycled in this manner three times. In all batches, yields of 97% of theory and purities of 97.7% were achieved.

EXAMPLE 8

Recycling Zinc Chloride and the Phase-transfer Catalyst TDA-HCl by Extraction with W/Methanol A 0.5 l three-neck glass flask equipped with paddle agitator, dropping funnel, reflux condenser and water sepa-

TABLE 5

| Ex. | x anhydrous ZnCl$_2$ [g] | y ZnCl$_2$ solution [g] | z conc. of the ZnCl$_2$ solution [% by wt.] | Yield [% of theory] | Purity [%] | Distillation residue [%] | Distillate color [C.I] |
|---|---|---|---|---|---|---|---|
| 6 | 125 | — | — | 98 | 97.2 | 2.1 | 13 |
| 6.1 | 14.2 | 128.6 | 86.1 | 97 | 97.7 | 1.0 | 15 |
| 6.2 | 8.3 | 135.8 | 86.0 | 97 | 97.8 | 0.7 | 15 |
| 6.3 | 5.0 | 141.0 | 85.2 | 97 | 97.8 | 0.6 | 20 |
| 6.4 | 3.0 | 144.7 | 84.6 | 97 | 97.6 | 0.6 | 18 |
| 6.6 | 2.0 | 142.1 | 88.1 | 94 | 97.1 | 2.6 | 19 |
| 6.6 | 12.4 | 132.6 | 85.0 | 98 | 97.6 | 0.9 | 17 |
| 6.7 | 6.0 | 140.1 | 84.9 | 97 | 97.7 | 0.9 | 16 |
| 6.8 | 2.0 | 146.6 | 84.5 | 97 | 97.6 | 0.8 | 19 |
| 6.9 | 1.4 | 146.2 | 84.6 | 97 | 97.6 | 0.7 | 13 |
| 6.10 | 5.0 | 142.9 | 84.0 | 90 | 96.5 | 1.8 | 23 |
| 6.11 | 3.2 | 144.9 | 84.0 | 94 | 97.0 | 2.2 | 16 |
| 6.12 | 4.7 | 142.2 | 84.6 | 93 | 97.4 | 1.1 | 15 |
| 6.13 | 5.3 | 142.6 | 83.9 | 97 | 97.5 | 0.7 | 18 |
| 6.14 | 1.0 | 147.7 | 84.0 | 96 | 97.5 | 1.3 | 17 |
| 6.15 | 2.4 | 145.1 | 84.5 | 93 | 97.0 | 3.4 | 15 |
| 6.16 | 6.3 | 141.4 | 83.9 | 97 | 97.5 | 0.8 | 13 |
| 6.17 | 7.7 | 139.4 | 84.1 | 96 | 97.6 | 1.0 | 19 |
| 6.18 | 2.6 | 146.0 | 83.8 | 96 | 97.5 | 1.8 | 15 |
| 6.19 | 6.4 | 144.0 | 83.9 | 96 | 97.5 | 1.0 | 16 |
| 6.20 | 4.2 | 144.0 | 83.9 | 97 | 97.4 | 0.7 | 17 | rator was charged with 150 g of heptane, 76 g of TMH, 1.5 g of TDA and 16 g of anhydrous ZnCl$_2$ and the batch was heated with stirring. Hydrogen chloride was added (approximately 5 g/h) and 153 g of IP were added to the boiling mixture. The batch was allowed to react for a further 1 h. After cooling, 100 ml of W and methanol each were added three times, the reaction mixture was mixed and, after standing, the phases were separated. The heptane phase was concentrated and the crude tocopherol was esterified to give VEA by refluxing with acetic anhydride.

The combined aqueous methanol phases were concentrated by evaporation and charged as catalyst for the next experiment. 150 g of heptane, 76 g of TMH and 1.6 g of fresh $ZnCl_2$ were added, the batch was heated with stirring as described above and hydrogen chloride was added (approximately 5 g/h). 153 g of IP were added to the boiling mixture. The batch was allowed to react for a further 1 h. The work-up was performed as described above.

The zinc chloride and TDA were recycled three times in this manner. All batches gave yields of VEA of about 97% of theory and purities of 97.7%.

This example shows that by extraction with a mixture of W and methanol in a ratio of about 1:1, not only the zinc chloride, but also the phase-transfer catalyst TDA.HCl can be recycled virtually completely to the process.

EXAMPLE 9

Repeated Recycling of Zinc Bromide

In a similar manner to Example 5, but adding 22 ml of a 47% strength by weight aqueous HBr solution instead of introducing HCl gas, 600 g of TMH in the presence of the amounts given by Table 6×[g] of anhydrous zinc bromide and y [g] of a recycled aqueous zinc bromide solution having a concentration of Z % by weight were reacted with 1210 g of IP to give α-tocopherol. After further reaction for 1 hour, the mixture was washed three times, each time with 100 ml of water, 98–100% of the zinc bromide used being recovered. After taking off the solvent, the crude α-tocopherol was esterified with acetic anhydride.

In this manner, from about 460 to 480 g of zinc bromide solution having a mean concentration of 37% by weight of zinc bromide were obtained each time. These solutions were filtered and concentrated on a Sambay evaporator. The concentrate was kept until reuse at 100° C., without it solidifying. As described above, it was used each time as catalyst for the following condensation batch.

The Examples 9 to 9.2 show that recycling the catalyst is also possible when zinc bromide is used, without impairing the yield or the purity of the vitamin E acetate, in the process according to the invention.

TABLE 6

| Ex. | x $ZnBr_2$ anhydrous [g] | y $ZnBr_2$ solution [g] | z concentration of the $ZnBr_2$ solution [% by wt.] | Yield [% of theory] | Purity [%] | Distillation residue [%] | Distillate color [C.I.] |
| --- | --- | --- | --- | --- | --- | --- | --- |
| 9 | 188.4 | — | — | 96 | 98.2 | 0.8 | 22 |
| 9.1 | 20.0 | 185.3 | 89.1 | 97 | 98.4 | 2.4 | 16 |
| 9.2 | 8.6 | 210.5 | 83.7 | 97 | 97.9 | 1.3 | 19 |

We claim:

1. A process for preparing α-tocopherol or α-tocopheryl acetate by reacting 2,3,5-trimethylhydroquinone with phytol or isophytol in the presence of a zinc halide condensation catalyst and a proton donor, optionally with subsequent esterification with acetic anhydride, which comprises A. carrying out the reaction in a nonpolar solvent and B. introducing the required zinc halide into the reaction in the form of a mixture of from 1 to 4 mol of water per mol of zinc halide.

2. A process for preparing α-tocopherol or α-tocopheryl acetate by reacting 2,3,5-trimethylhydroquinone with phytol or isophytol in the presence of a mixture of water and zinc chloride or zinc bromide and a proton donor in a solvent, optionally with subsequent esterification with acetic anhydride, which comprises A. carrying out the reaction in a nonpolar solvent, B. after completing the reaction, either separating off the zinc chloride or zinc bromide, extracting the zinc chloride or zinc bromide from the resulting tocopherol solution with water or a mixture of water and a low-boiling water-miscible organic solvent, or both separating and extracting the zinc chloride or zinc bromide and C. optionally concentrating the zinc chloride or zinc bromide solution resulting from process step B. and recycling the zinc chloride or zinc bromide solution to the reaction process, in the form of a from about 60 to 90% strength by weight optionally hot solution or pumpable magma in such a manner that, after adding zinc chloride or zinc bromide as necessary, not more than 4 mol of water per mol of zinc chloride or zinc bromide are present in the reaction mixture.

3. A process as claimed in claim 1 or 2, wherein the nonpolar solvent is hexane, heptane, cyclohexane, octane, nonane, decane, toluene, xylene or a mixture of 2 or more of these solvents.

4. A process as claimed in claim 2, wherein in process step B. the majority of the zinc chloride or zinc bromide is extracted from the tocopherol solution using water or a mixture of water and methanol and in process step C. sufficient of the hot solution or pumpable magma is recycled to the reaction process so that, after adding zinc chloride or zinc bromide as necessary, using anhydrous zinc chloride or zinc bromide or a from 85 to 90% strength by weight solution or pumpable magma, not more than 3 mol of water per mol of zinc chloride or zinc bromide are present in the reaction mixture.

5. A process as claimed in claim 2, wherein in process step B. the zinc chloride or zinc bromide is removed as completely as possible from the tocopherol solution by repeated extraction with water or a mixture of water and methanol and optionally about 1% by weight of added HCl and in process step C. the zinc chloride or zinc bromide solution obtained in process step B is concentrated by evaporating water or methanol and water so that the solution recycled to the reaction process has no more than 3 mol of water per mol of zinc chloride or zinc bromide.

6. A process as claimed in claim 5, wherein in process step C the zinc chloride or zinc bromide solution is concentrated in a special distillation apparatus optionally in the presence of a suitable compound capable of forming an azeotropic mixture, before it is recycled to the reaction process.

7. A process as claimed in claim 5, wherein in process step C. the zinc chloride or zinc bromide solution is concentrated in the reaction vessel itself prior to the addition of isophytol optionally in the presence of the solvent used for the reaction.

8. A process as claimed in claim 2, wherein, in process step B. after completing the reaction, the zinc chloride or zinc bromide, together with any ammonium salt, amine or ammonium salt and amine and unreacted trimethylhydroquinone present are extracted from the resulting tocopherol solution using a mixture of water and methanol in a weight ratio of from about 4:1 to 1:10 and in process step C. the resulting extract, after concentration in the form of a optionally hot solution or pumpable magna, is recycled to the reaction process in such a manner that, in the reaction mixture, after adding zinc chloride or zinc bromide as necessary, not more than 3 mol of water per mol of zinc chloride or zinc bromide are present.

9. A process as claimed in claim 2, wherein in process step C the zinc chloride or zinc bromide solution is concentrated to contain no more than 3 mol of water per mol of zinc chloride or zinc bromide.

10. A process for preparing $\alpha$-tocopherol or $\alpha$-tocopheryl acetate by reacting 2,3,5-trimethylhydroquinone with phytol or isophytol in the presence of a mixture of water and a zinc halide condensation catalyst and a proton donor, optionally with subsequent esterification with acetic anhydride, which comprises A. carrying out the reaction in a nonpolar solvent and B. introducing the required zinc halide into the reaction in the form of a mixture of not more than about 4 mol of water per mol of zinc halide.

11. The process as claimed in claim 10, wherein the zinc halide is introduced into the reaction mixture in the form of a mixture of not more than about 3 mol of water per mol of zinc halide.

12. A process as claimed in claim 10, wherein, after the reaction is complete, the zinc halide is recycled to the reaction process in the form of a from about 60 to 90% strength by weight solution or pumpable magma such that not more than about 4 mol of water per mol of zinc halide are present in the reaction mixture.

* * * * *

UNITED STATES PATENT AND TRADEMARK OFFICE
CERTIFICATE OF CORRECTION

PATENT NO. : 6,005,122

DATED : December 21, 1999

INVENTOR(S): Kai-Uwe BALDENIUS et al.

It is certified that an error appears in the above-identified patent and that said Letters Patent is hereby corrected as shown below:

On the title page, item [30], the Foreign Application Priority Data has been omitted. It should read as follows:

--[30] Foreign Application Priority Data

Dec. 23, 1996 [DE] Germany...................196 54 038
Aug. 1, 1997 [DE] Germany...................197 33 503--

Signed and Sealed this

Twenty-fourth Day of April, 2001

Attest:

NICHOLAS P. GODICI

*Attesting Officer*   *Acting Director of the United States Patent and Trademark Office*